(12) United States Patent
Vitello (10) Patent No.: US 11,857,751 B1
(45) Date of Patent: Jan. 2, 2024

(54) ASSEMBLY FOR A MEDICAL CONNECTOR

(71) Applicant: INTERNATIONAL MEDICAL INDUSTRIES INC., Pompano Beach, FL (US)

(72) Inventor: Patrick Vitello, Pompano Beach, FL (US)

(73) Assignee: INTERNATIONAL MEDICAL INDUSTRIES INC., Pompano Beach, FL (US)

( * ) Notice: Subject to any disclaimer, the term of this patent is extended or adjusted under 35 U.S.C. 154(b) by 276 days.

(21) Appl. No.: 16/459,981

(22) Filed: Jul. 2, 2019

Related U.S. Application Data (60) Provisional application No. 62/693,207, filed on Jul. 2, 2018.

(51) Int. Cl.
*A61M 39/10* (2006.01)
*A61M 39/20* (2006.01)
*A61M 5/50* (2006.01)

(52) U.S. Cl.
CPC ...... *A61M 39/1011* (2013.01); *A61M 5/5086* (2013.01); *A61M 39/20* (2013.01); *A61M 2039/1066* (2013.01)

(58) Field of Classification Search
CPC A61M 39/1011; A61M 5/5086; A61M 39/20; A61M 2039/1066; A61M 2005/312; A61M 2005/3104; A61M 5/3202; A61M 2004/3104; A61M 5/50; A61M 39/101; A61M 2205/273; B65D 51/002; B65D 51/18
See application file for complete search history.

(56) References Cited

U.S. PATENT DOCUMENTS 722,943 A 3/1903 Chappell
732,662 A 6/1903 Smith
(Continued)

FOREIGN PATENT DOCUMENTS

DE 202008018507 2/2015
EP 0148116 A 7/1985
(Continued)

OTHER PUBLICATIONS

Arai Tsugio; Jan. 1996, Machine translation of JPH-082544-A (Year: 1996).*

*Primary Examiner* — Katherine H Schwiker
*Assistant Examiner* — Robert F Allen
(74) *Attorney, Agent, or Firm* — MALLOY AND MALLOY PL; Jennie Sue Malloy (57) ABSTRACT

A closure assembly for a medical dispenser having tamper evident characteristics including a flexible tip cap dimensioned to be independently used with different sized medical dispensers. The tip cap is operatively disposed in enclosing relation to a discharge port of the medical dispenser and a retainer is disposed in surrounding relation to said tip cap concurrent to the operative disposition thereof relative to the discharge port. The retainer includes a clamping structure disposed in clamping relation to an exterior of said tip cap, wherein the clamping relation disposes the interior of the tip cap into fluid sealing engagement with the discharge port. After removal of the discharge port, reinsertion thereof is prevented by deformation of the tip cap into an insertion blocking concurrent to maintenance the clamping relation.

10 Claims, 4 Drawing Sheets

(56) References Cited

U.S. PATENT DOCUMENTS

| | | |
|---|---|---|
| 1,678,991 A | 7/1928 | Marschalek |
| 1,970,631 A | 8/1934 | Sherman |
| 2,477,598 A | 8/1949 | Hain |
| 2,739,590 A | 3/1956 | Yochem |
| 2,823,674 A | 2/1958 | Yochem |
| 2,834,346 A | 5/1958 | Adams |
| 2,875,761 A | 3/1959 | Helmer et al. |
| 2,888,015 A | 5/1959 | Hunt |
| 2,952,255 A | 9/1960 | Hein, Jr. |
| 3,122,280 A | 2/1964 | Goda |
| 3,245,567 A | 4/1966 | Knight |
| 3,323,798 A | 6/1967 | Miller |
| 3,364,890 A | 1/1968 | Andersen |
| 3,489,268 A | 1/1970 | Meierhoefer |
| 3,368,673 A | 3/1971 | Cowley |
| 3,574,306 A | 4/1971 | Alden |
| 3,598,120 A | 8/1971 | Mass |
| 3,610,241 A | 10/1971 | LeMarie |
| 3,674,181 A | 7/1972 | Marks et al. |
| 3,700,215 A | 10/1972 | Hardman et al. |
| 3,706,307 A | 12/1972 | Hasson |
| 3,712,749 A | 1/1973 | Roberts |
| 3,726,445 A | 4/1973 | Ostrowsky et al. |
| 3,747,751 A | 7/1973 | Miller et al. |
| 3,850,329 A | 11/1974 | Robinson |
| 3,872,867 A | 3/1975 | Killinger |
| 3,904,033 A | 9/1975 | Haerr |
| 3,905,375 A | 9/1975 | Toyama |
| 3,937,211 A | 2/1976 | Merten |
| 3,987,930 A | 10/1976 | Fuson |
| 4,005,739 A | 2/1977 | Winchell |
| 4,043,334 A | 8/1977 | Brown et al. |
| 4,046,145 A | 9/1977 | Choksi et al. |
| 4,068,696 A | 1/1978 | Winchell |
| 4,106,621 A | 8/1978 | Sorenson |
| 4,216,585 A | 8/1980 | Hatter |
| 4,216,872 A | 8/1980 | Bean |
| 4,244,366 A | 1/1981 | Raines |
| 4,252,122 A | 2/1981 | Halvorsen |
| 4,271,972 A | 6/1981 | Thor |
| 4,286,591 A | 9/1981 | Raines |
| 4,286,640 A | 9/1981 | Knox et al. |
| 4,313,539 A | 2/1982 | Raines |
| 4,369,781 A | 1/1983 | Gilson et al. |
| 4,420,085 A | 12/1983 | Wilson et al. |
| 4,430,077 A | 2/1984 | Mittleman et al. |
| 4,457,445 A | 7/1984 | Hanks et al. |
| 4,482,071 A | 11/1984 | Ishiwatari |
| D277,783 S | 2/1985 | Beck |
| 4,521,237 A | 6/1985 | Logothetis |
| 4,530,697 A | 7/1985 | Kuhlemann et al. |
| 4,571,242 A | 2/1986 | Klein et al. |
| 4,589,171 A | 5/1986 | McGill |
| 4,664,259 A | 5/1987 | Landis |
| 4,667,837 A | 5/1987 | Vitello et al. |
| 4,676,530 A | 6/1987 | Nordgren et al. |
| 4,693,707 A | 9/1987 | Dye |
| 4,726,483 A | 2/1988 | Drozd |
| 4,735,617 A | 4/1988 | Nelson et al. |
| 4,742,910 A | 5/1988 | Staebler |
| 4,743,229 A | 5/1988 | Chu |
| 4,743,231 A | 5/1988 | Kay et al. |
| 4,760,847 A | 8/1988 | Vaillancourt |
| 4,813,564 A | 3/1989 | Cooper et al. |
| 4,832,695 A | 5/1989 | Rosenberg et al. |
| 4,834,706 A | 5/1989 | Beck et al. |
| 4,842,592 A | 6/1989 | Caggiani et al. |
| 4,844,906 A | 7/1989 | Hermelin et al. |
| 4,906,231 A | 3/1990 | Young |
| 4,919,285 A | 4/1990 | Roof et al. |
| 4,936,445 A | 6/1990 | Grabenkort |
| 5,009,323 A | 4/1991 | Montgomery et al. |
| 5,024,323 A | 6/1991 | Bolton |
| 5,049,129 A | 9/1991 | Zdeb et al. |
| 5,057,093 A | 10/1991 | Clegg et al. |
| D323,392 S | 1/1992 | Byrne |
| 5,078,696 A | 1/1992 | Nedbaluk |
| 5,085,332 A | 2/1992 | Gettig et al. |
| 5,090,564 A | 2/1992 | Chimienti |
| 5,133,454 A | 7/1992 | Hammer |
| 5,135,496 A | 8/1992 | Vetter et al. |
| 5,163,922 A | 11/1992 | McElveen, Jr. et al. |
| 5,165,560 A | 11/1992 | Enniss, III et al. |
| 5,230,429 A | 7/1993 | Etheredge, III |
| 5,267,983 A | 12/1993 | Oilschlager et al. |
| 5,292,308 A | 3/1994 | Ryan |
| 5,293,993 A | 3/1994 | Yates, Jr. et al. |
| 5,295,599 A | 3/1994 | Smith |
| 5,312,367 A | 5/1994 | Nathan |
| 5,312,368 A | 5/1994 | Haynes |
| 5,328,466 A | 7/1994 | Denmark |
| 5,328,474 A | 7/1994 | Raines |
| 5,356,380 A | 10/1994 | Hoekwater et al. |
| 5,370,226 A | 12/1994 | Gollobin et al. |
| 5,380,295 A | 1/1995 | Vacca |
| 5,402,887 A | 4/1995 | Shillington |
| 5,405,339 A | 4/1995 | Kohnen et al. |
| 5,456,668 A | 10/1995 | Ogle, II |
| 5,458,580 A | 10/1995 | Hajishoreh |
| 5,468,224 A | 11/1995 | Souryal |
| 5,474,178 A | 12/1995 | DiViesti et al. |
| 5,505,705 A | 4/1996 | Galpin et al. |
| 5,531,695 A | 7/1996 | Swisher |
| 5,540,666 A | 7/1996 | Barta et al. |
| 5,549,571 A | 8/1996 | Sak |
| 5,558,648 A | 9/1996 | Shields |
| 5,584,817 A | 12/1996 | van den Haak |
| 5,588,239 A | 12/1996 | Anderson |
| 5,624,402 A | 4/1997 | Imbert |
| 5,662,233 A | 9/1997 | Reid |
| 5,674,209 A | 10/1997 | Yarger |
| 5,695,470 A | 12/1997 | Roussigne et al. |
| 5,700,247 A | 12/1997 | Grimard et al. |
| 5,702,374 A | 12/1997 | Johnson |
| 5,713,485 A | 2/1998 | Liff et al. |
| 5,776,124 A | 7/1998 | Wald |
| 5,785,691 A | 7/1998 | Vetter et al. |
| 5,797,885 A | 8/1998 | Rubin |
| 5,807,343 A | 9/1998 | Tucker et al. |
| D402,766 S | 12/1998 | Smith et al. |
| 5,842,567 A | 12/1998 | Rowe et al. |
| 5,876,381 A | 3/1999 | Pond et al. |
| 5,883,806 A | 3/1999 | Meador et al. |
| 5,884,457 A | 3/1999 | Ortiz et al. |
| 5,902,269 A | 5/1999 | Jentzen |
| 5,926,922 A | 7/1999 | Stottle |
| 5,951,522 A | 9/1999 | Rosato et al. |
| 5,951,525 A | 9/1999 | Thorne et al. |
| 5,954,657 A | 9/1999 | Rados |
| 5,957,166 A | 9/1999 | Safabash |
| 5,957,314 A | 9/1999 | Nishida et al. |
| 5,963,136 A | 10/1999 | O'Brien |
| 5,989,227 A | 11/1999 | Vetter et al. |
| 5,993,437 A | 11/1999 | Raoz |
| 6,000,548 A | 12/1999 | Tsals |
| D419,671 S | 1/2000 | Jansen |
| 6,021,824 A | 2/2000 | Larsen et al. |
| 6,027,482 A | 2/2000 | Imbert |
| 6,068,614 A | 5/2000 | Kimber et al. |
| D430,293 S | 8/2000 | Jansen |
| D431,864 S | 10/2000 | Jansen |
| 6,126,640 A | 10/2000 | Tucker et al. |
| 6,190,364 B1 | 2/2001 | Imbert |
| 6,193,688 B1 | 2/2001 | Balestracci et al. |
| 6,196,593 B1 | 3/2001 | Petrick et al. |
| 6,196,998 B1 | 3/2001 | Jansen et al. |
| 6,216,885 B1 | 4/2001 | Guillaume |
| 6,279,746 B1 | 4/2001 | Hussaini et al. |
| 6,235,376 B1 | 5/2001 | Miyazaki et al. |
| 6,280,418 B1 | 8/2001 | Reinhard et al. |
| 6,287,671 B1 | 9/2001 | Bright et al. |
| 6,322,543 B1 | 11/2001 | Singh et al. |
| 6,338,200 B1 | 1/2002 | Baxa et al. |
| 6,358,241 B1 | 3/2002 | Shapeton et al. |

(56) References Cited

U.S. PATENT DOCUMENTS

| | | |
|---|---|---|
| 6,375,640 B1 | 4/2002 | Teraoka |
| 6,394,983 B1 | 5/2002 | Mayoral et al. |
| 6,439,276 B1 | 8/2002 | Wood et al. |
| 6,485,460 B2 | 11/2002 | Eakins et al. |
| 6,488,666 B1 | 12/2002 | Geist |
| 6,491,665 B1 | 12/2002 | Vetter et al. |
| 6,500,155 B2 | 12/2002 | Sasso |
| 6,520,935 B1 | 2/2003 | Jansen et al. |
| 6,540,697 B2 | 4/2003 | Chen |
| 6,565,529 B1 | 5/2003 | Kimber et al. |
| 6,581,792 B1 | 6/2003 | Limanjaya |
| 6,585,691 B1 | 7/2003 | Vitello |
| 6,592,251 B2 | 7/2003 | Edwards et al. |
| 6,666,852 B2 | 12/2003 | Niedospial, Jr. |
| 6,682,798 B1 | 1/2004 | Kiraly |
| 6,726,652 B2 | 4/2004 | Eakins et al. |
| 6,726,672 B1 | 4/2004 | Hanley et al. |
| 6,755,220 B2 | 6/2004 | Castellano et al. |
| 6,764,469 B2 | 7/2004 | Broselow |
| 6,796,586 B2 | 9/2004 | Werth |
| 6,821,268 B2 | 11/2004 | Balestracci |
| D501,549 S | 2/2005 | McAllister et al. |
| 6,921,383 B2 | 7/2005 | Vitello |
| 6,935,560 B2 | 8/2005 | Andreasson et al. |
| 6,942,643 B2 | 9/2005 | Eakins et al. |
| 7,036,661 B2 | 5/2006 | Anthony et al. |
| 7,055,273 B2 | 6/2006 | Roshkoff |
| 7,100,771 B2 | 9/2006 | Massengale et al. |
| 7,125,397 B2 | 10/2006 | Woehr et al. |
| 7,141,286 B1 | 11/2006 | Kessler et al. |
| 7,175,081 B2 | 2/2007 | Andreasson et al. |
| 7,182,256 B2 | 2/2007 | Andreasson et al. |
| 7,232,066 B2 | 6/2007 | Andreasson et al. |
| 7,240,926 B2 | 7/2007 | Dalle et al. |
| 7,299,981 B2 | 11/2007 | Hickle et al. |
| 7,374,555 B2 | 5/2008 | Heinz et al. |
| 7,404,500 B2 | 7/2008 | Marteau et al. |
| 7,410,803 B2 | 8/2008 | Nollert et al. |
| 7,425,208 B1 | 9/2008 | Vitello |
| 7,437,972 B2 | 10/2008 | Yeager |
| D581,046 S | 11/2008 | Sudo |
| D581,047 S | 11/2008 | Koshidaka |
| D581,049 S | 11/2008 | Sudo |
| 7,482,166 B2 | 1/2009 | Nollert et al. |
| D589,612 S | 3/2009 | Sudo |
| 7,497,330 B2 | 3/2009 | Anthony et al. |
| 7,503,453 B2 | 3/2009 | Cronin et al. |
| 7,588,563 B2 | 9/2009 | Guala |
| 7,594,681 B2 | 9/2009 | DeCarlo |
| 7,608,057 B2 | 10/2009 | Woehr et al. |
| 7,611,487 B2 | 11/2009 | Woehr et al. |
| 7,632,244 B2 | 12/2009 | Buehler et al. |
| D608,900 S | 1/2010 | Giraud et al. |
| 7,641,636 B2 | 1/2010 | Moesli et al. |
| D612,939 S | 3/2010 | Boone, III et al. |
| 7,681,606 B2 | 3/2010 | Khan et al. |
| 7,698,180 B2 | 4/2010 | Fago et al. |
| 7,735,664 B1 | 6/2010 | Peters et al. |
| 7,748,892 B2 | 7/2010 | McCoy |
| 7,762,988 B1 | 7/2010 | Vitello |
| 7,766,919 B2 | 8/2010 | Delmotte |
| 7,802,313 B2 | 9/2010 | Czajka |
| 7,886,908 B2 | 2/2011 | Farrar et al. |
| 7,918,830 B2 | 4/2011 | Langan et al. |
| 7,922,213 B2 | 4/2011 | Werth |
| 8,034,041 B2 | 10/2011 | Domkowski |
| 8,079,518 B2 | 12/2011 | Turner et al. |
| 8,091,727 B2 | 1/2012 | Domkowski |
| 8,118,788 B2 | 2/2012 | Frezza |
| 8,137,324 B2 | 3/2012 | Bobst |
| 8,140,349 B2 | 3/2012 | Hanson et al. |
| 8,252,247 B2 | 8/2012 | Ferlic |
| 8,257,286 B2 | 9/2012 | Meyer et al. |
| 8,328,082 B1 | 12/2012 | Bochenko et al. |
| 8,348,895 B1 | 1/2013 | Vitello |
| 8,353,869 B2 * | 1/2013 | Ranalletta ............... A61J 1/18 |
| | | 604/111 |
| 8,413,811 B1 | 4/2013 | Arendt |
| 8,443,999 B1 | 5/2013 | Reinders |
| D684,057 S | 6/2013 | Kwon |
| 8,512,277 B2 | 8/2013 | Del Vecchio |
| 8,528,757 B2 | 9/2013 | Bisio |
| 8,556,074 B2 | 10/2013 | Turner et al. |
| 8,579,116 B2 | 11/2013 | Pether et al. |
| 8,591,462 B1 | 11/2013 | Vitello |
| 8,597,255 B2 | 12/2013 | Emmott et al. |
| 8,597,271 B2 | 12/2013 | Langan et al. |
| 8,616,413 B2 | 12/2013 | Koyama |
| D701,304 S | 3/2014 | Lair et al. |
| 8,672,902 B2 | 3/2014 | Ruan et al. |
| 8,702,674 B2 | 4/2014 | Bochenko |
| 8,777,910 B2 | 7/2014 | Bauss et al. |
| 8,777,930 B2 | 7/2014 | Swisher et al. |
| 8,852,561 B2 | 10/2014 | Wagner et al. |
| 8,864,021 B1 | 10/2014 | Vitello |
| 8,864,707 B1 | 10/2014 | Vitello |
| 8,864,708 B1 | 10/2014 | Vitello |
| 8,911,424 B2 | 12/2014 | Weadock et al. |
| 8,945,082 B2 | 2/2015 | Geiger et al. |
| 9,016,473 B2 | 4/2015 | Tamarindo |
| 9,082,157 B2 | 7/2015 | Gibson |
| 9,101,534 B2 | 8/2015 | Bochenko |
| D738,495 S | 9/2015 | Strong et al. |
| 9,125,976 B2 | 9/2015 | Uber, III et al. |
| D743,019 S | 11/2015 | Schultz |
| 9,199,042 B2 | 12/2015 | Farrar et al. |
| 9,199,749 B1 | 12/2015 | Vitello |
| 9,220,486 B2 | 12/2015 | Schweiss et al. |
| 9,220,577 B2 | 12/2015 | Jessop et al. |
| 9,227,019 B2 | 1/2016 | Swift et al. |
| D750,228 S | 2/2016 | Strong et al. |
| 9,272,099 B2 | 3/2016 | Limaye et al. |
| 9,311,592 B1 | 4/2016 | Vitello et al. |
| D756,777 S | 5/2016 | Berge et al. |
| 9,336,669 B2 | 5/2016 | Bowden et al. |
| D759,486 S | 6/2016 | Ingram et al. |
| D760,384 S | 6/2016 | Niunoya et al. |
| D760,902 S | 7/2016 | Persson |
| 9,402,967 B1 | 8/2016 | Vitello |
| 9,427,715 B2 | 8/2016 | Palazzolo et al. |
| 9,433,768 B2 | 9/2016 | Tekeste et al. |
| 9,463,310 B1 | 10/2016 | Vitello |
| D773,043 S | 11/2016 | Insgram et al. |
| D777,903 S | 3/2017 | Schultz |
| 9,662,456 B2 | 5/2017 | Woehr |
| D789,529 S | 6/2017 | Davis et al. |
| 9,687,249 B2 | 6/2017 | Hanlon et al. |
| 9,744,304 B2 | 8/2017 | Swift et al. |
| D797,928 S | 9/2017 | Davis et al. |
| D797,929 S | 9/2017 | Davis et al. |
| 9,764,098 B2 | 9/2017 | Hund et al. |
| 9,821,152 B1 | 11/2017 | Vitello et al. |
| D806,241 S | 12/2017 | Swinney et al. |
| D807,503 S | 1/2018 | Davis et al. |
| 9,855,191 B1 | 1/2018 | Vitello et al. |
| D815,945 S | 4/2018 | Fischer |
| 9,987,438 B2 | 6/2018 | Stillson |
| D825,746 S | 8/2018 | Davis et al. |
| 10,039,913 B2 | 8/2018 | Yeh |
| D831,201 S | 10/2018 | Holtz et al. |
| D820,187 S | 11/2018 | Ryan |
| 10,124,122 B2 | 11/2018 | Zenker |
| 10,166,343 B1 | 1/2019 | Hunt et al. |
| 10,166,347 B1 | 1/2019 | Vitello |
| 10,183,129 B1 | 1/2019 | Vitello |
| 10,207,099 B1 | 2/2019 | Vitello |
| D842,464 S | 3/2019 | Davis et al. |
| D847,373 S | 4/2019 | Hurwit et al. |
| 10,300,263 B1 | 5/2019 | Hunt |
| 10,307,548 B1 | 6/2019 | Hunt et al. |
| 10,315,024 B1 * | 6/2019 | Vitello .............. A61M 39/1055 |
| 10,315,808 B2 | 6/2019 | Taylor et al. |
| 10,376,655 B2 | 8/2019 | Pupke et al. |
| D859,125 S | 9/2019 | Weagle et al. |

(56) References Cited

U.S. PATENT DOCUMENTS

| | | |
|---|---|---|
| 10,478,262 B2 | 11/2019 | Niese et al. |
| 10,758,684 B1 | 9/2020 | Vitello et al. |
| 10,773,067 B2 | 9/2020 | Davis et al. |
| 10,898,659 B1 | 1/2021 | Vitello et al. |
| 10,912,898 B1 | 2/2021 | Vitello et al. |
| 10,933,202 B1 | 3/2021 | Banik |
| 10,953,162 B1 | 3/2021 | Hunt et al. |
| 11,040,149 B1 | 6/2021 | Banik |
| 11,040,154 B1 | 6/2021 | Vitello et al. |
| 11,097,071 B1 | 8/2021 | Hunt et al. |
| 11,278,681 B1 | 3/2022 | Banik et al. |
| D948,713 S | 4/2022 | Banik |
| 11,357,588 B1 | 6/2022 | Vitello et al. |
| 11,413,406 B1 | 8/2022 | Vitello et al. |
| 11,426,328 B1 | 8/2022 | Ollmann et al. |
| 11,471,610 B1 | 10/2022 | Banik et al. |
| 11,523,970 B1 | 12/2022 | Vitello et al. |
| 11,541,180 B1 | 1/2023 | Vitello et al. |
| 11,690,994 B1 | 7/2023 | Banik et al. |
| 11,697,527 B1 | 7/2023 | Hendren et al. |
| 2001/0003150 A1 | 6/2001 | Imbert |
| 2001/0034506 A1 | 10/2001 | Hirschman et al. |
| 2001/0056258 A1 | 12/2001 | Evans |
| 2002/0007147 A1 | 1/2002 | Capes et al. |
| 2002/0023409 A1 | 2/2002 | Py |
| 2002/0046962 A1 | 4/2002 | Vallans et al. |
| 2002/0079281 A1 | 6/2002 | Hierzer et al. |
| 2002/0097396 A1 | 7/2002 | Schafer |
| 2002/0099334 A1 | 7/2002 | Hanson et al. |
| 2002/0101656 A1 | 8/2002 | Blumenthal et al. |
| 2002/0104770 A1 | 8/2002 | Shapeton et al. |
| 2002/0133119 A1 | 9/2002 | Eakins et al. |
| 2003/0055685 A1 | 3/2003 | Cobb et al. |
| 2003/0146617 A1 | 8/2003 | Franko, Sr. |
| 2003/0183547 A1 | 10/2003 | Heyman |
| 2003/0187403 A1 | 10/2003 | Balestracci |
| 2004/0008123 A1 | 1/2004 | Carrender et al. |
| 2004/0064095 A1 | 4/2004 | Vitello |
| 2004/0116858 A1 | 6/2004 | Heinz et al. |
| 2004/0173563 A1 | 9/2004 | Kim et al. |
| 2004/0186437 A1 | 9/2004 | Frenette et al. |
| 2004/0225258 A1 | 11/2004 | Balestracci |
| 2005/0146081 A1 | 7/2005 | MacLean et al. |
| 2005/0148941 A1 | 7/2005 | Farrar et al. |
| 2005/0209555 A1 | 9/2005 | Middleton et al. |
| 2006/0084925 A1 | 4/2006 | Ramsahoye |
| 2006/0089601 A1 | 4/2006 | Dionigi |
| 2006/0169611 A1 | 8/2006 | Prindle |
| 2006/0173415 A1 | 8/2006 | Cummins |
| 2006/0189933 A1 | 8/2006 | Alheidt et al. |
| 2007/0060898 A1 | 3/2007 | Shaughnessy et al. |
| 2007/0106234 A1 | 5/2007 | Klein |
| 2007/0142786 A1 | 6/2007 | Lampropoulos et al. |
| 2007/0191690 A1 | 8/2007 | Hasse et al. |
| 2007/0219503 A1 | 9/2007 | Loop et al. |
| 2007/0257111 A1 | 11/2007 | Ortenzi |
| 2008/0068178 A1 | 3/2008 | Meyer |
| 2008/0097310 A1* | 4/2008 | Buehler .................. A61M 5/50 |
| | | 604/111 |
| 2008/0106388 A1 | 5/2008 | Knight |
| 2008/0140020 A1 | 6/2008 | Shirley |
| 2008/0243088 A1 | 10/2008 | Evans |
| 2008/0303267 A1 | 12/2008 | Schnell et al. |
| 2008/0306443 A1 | 12/2008 | Neer |
| 2009/0084804 A1 | 4/2009 | Caspary |
| 2009/0099552 A1 | 4/2009 | Levy et al. |
| 2009/0149815 A1 | 6/2009 | Kiel et al. |
| 2009/0166311 A1 | 7/2009 | Claessens |
| 2009/0326481 A1 | 12/2009 | Swisher et al. |
| 2010/0050351 A1* | 3/2010 | Colantonio ............... A61L 2/18 |
| | | 15/104.93 |
| 2010/0084403 A1 | 4/2010 | Popish et al. |
| 2010/0126894 A1 | 5/2010 | Koukol et al. |
| 2010/0179822 A1 | 7/2010 | Reppas |
| 2010/0228226 A1 | 9/2010 | Nielsen |
| 2010/0252564 A1 | 10/2010 | Martinez et al. |
| 2010/0283238 A1 | 11/2010 | Deighan et al. |
| 2011/0044850 A1 | 2/2011 | Solomon et al. |
| 2011/0046550 A1 | 2/2011 | Schiller et al. |
| 2011/0046603 A1 | 2/2011 | Felsovalyi et al. |
| 2012/0064515 A2 | 3/2012 | Knapp et al. |
| 2012/0096957 A1 | 4/2012 | Ochman |
| 2012/0110950 A1 | 5/2012 | Schraudolph |
| 2013/0018356 A1 | 1/2013 | Prince et al. |
| 2013/0056130 A1 | 3/2013 | Alpert et al. |
| 2013/0088354 A1 | 4/2013 | Thomas |
| 2013/0237949 A1 | 9/2013 | Miller |
| 2013/0269592 A1 | 10/2013 | Heacock et al. |
| 2014/0000781 A1 | 1/2014 | Franko, Jr. |
| 2014/0034536 A1 | 2/2014 | Reinhardt et al. |
| 2014/0069202 A1 | 3/2014 | Fisk |
| 2014/0069829 A1 | 3/2014 | Evans |
| 2014/0076840 A1 | 3/2014 | Graux et al. |
| 2014/0135738 A1 | 5/2014 | Panian |
| 2014/0155868 A1 | 6/2014 | Nelson et al. |
| 2014/0163465 A1 | 6/2014 | Bartlett, II et al. |
| 2014/0257843 A1 | 9/2014 | Adler et al. |
| 2014/0326727 A1 | 11/2014 | Jouin |
| 2014/0353196 A1 | 12/2014 | Key |
| 2015/0013811 A1 | 1/2015 | Carrel et al. |
| 2015/0048045 A1 | 2/2015 | Miceli et al. |
| 2015/0112296 A1 | 4/2015 | Ishiwata et al. |
| 2015/0136632 A1 | 5/2015 | Moir et al. |
| 2015/0182686 A1 | 7/2015 | Okihara |
| 2015/0191633 A1 | 7/2015 | De Boer et al. |
| 2015/0246185 A1 | 9/2015 | Heinz |
| 2015/0302232 A1* | 10/2015 | Strassburger ...... B65D 43/0235 |
| | | 340/10.1 |
| 2015/0305982 A1 | 10/2015 | Bochenko |
| 2015/0310771 A1 | 10/2015 | Atkinson et al. |
| 2016/0067144 A1 | 3/2016 | Chang |
| 2016/0067422 A1* | 3/2016 | Davis .................. A61M 5/3134 |
| | | 604/192 |
| 2016/0090456 A1 | 3/2016 | Ishimaru et al. |
| 2016/0136352 A1 | 5/2016 | Smith et al. |
| 2016/0144119 A1 | 5/2016 | Limaye et al. |
| 2016/0158110 A1 | 6/2016 | Swisher et al. |
| 2016/0158449 A1 | 6/2016 | Limaye et al. |
| 2016/0176550 A1 | 6/2016 | Vitello et al. |
| 2016/0194121 A1 | 7/2016 | Ogawa et al. |
| 2016/0250420 A1* | 9/2016 | Maritan ............... A61M 5/3202 |
| | | 604/192 |
| 2016/0279032 A1 | 9/2016 | Davis |
| 2016/0328586 A1 | 11/2016 | Bowden et al. |
| 2016/0361235 A1 | 12/2016 | Swisher |
| 2016/0367439 A1 | 12/2016 | Davis et al. |
| 2017/0007771 A1 | 1/2017 | Duinat et al. |
| 2017/0014310 A1 | 1/2017 | Hyun et al. |
| 2017/0124289 A1 | 5/2017 | Hasan et al. |
| 2017/0173321 A1 | 6/2017 | Davis et al. |
| 2017/0203086 A1 | 7/2017 | Davis |
| 2017/0225843 A1 | 8/2017 | Glaser et al. |
| 2017/0239141 A1 | 8/2017 | Davis et al. |
| 2017/0297781 A1 | 10/2017 | Kawamura |
| 2017/0319438 A1 | 11/2017 | Davis et al. |
| 2017/0354792 A1 | 12/2017 | Ward |
| 2018/0001540 A1 | 1/2018 | Byun |
| 2018/0014998 A1 | 1/2018 | Yuki et al. |
| 2018/0064604 A1 | 3/2018 | Drmanovic |
| 2018/0078684 A1 | 3/2018 | Peng et al. |
| 2018/0089593 A1 | 3/2018 | Patel et al. |
| 2018/0098915 A1 | 4/2018 | Rajagopal et al. |
| 2018/0147115 A1 | 5/2018 | Nishioka et al. |
| 2018/0312305 A1 | 11/2018 | Rognard |
| 2019/0308006 A1 | 10/2019 | Erekovcanski et al. |
| 2019/0388626 A1 | 12/2019 | Okihara |
| 2022/0008645 A1 | 1/2022 | Ukai et al. |

FOREIGN PATENT DOCUMENTS

| | | |
|---|---|---|
| GB | 486367 | 6/1938 |
| JP | 08002544 A * | 1/1996 |
| WO | WO 2008/000279 | 1/2008 |
| WO | WO 2017086607 | 5/2015 |

(56) References Cited

FOREIGN PATENT DOCUMENTS

* cited by examiner

ASSEMBLY FOR A MEDICAL CONNECTOR

CLAIM OF PRIORITY

The present Non-Provisional patent application claims priority pursuant to 35 U.S.C. Section 119(e) to a prior filed Provisional patent application, namely, that having Ser. No. 62/693,207 filed on Jul. 2, 2018, the contents of which is incorporated herein by reference in its entirety.

FIELD OF THE INVENTION

This invention is directed to a closure assembly for a medical dispenser including a tip cap operatively disposed in enclosing relation to a discharge port of the medical dispenser. The tip cap includes sufficient flexibility to be forced into sealing engagement with the discharge port upon an appropriate clamping or deformation force being exerted on the exterior thereof.

DESCRIPTION OF THE RELATED ART

In the medical field, it is a common procedure for authorized medical personnel to order medicine or other substances to be administered to a patient whether orally, by an injection or intravenously through an IV. It is also a relatively common procedure for a number of administering devices, such as a syringe, to be pre-filled by authorized personnel whether within the hospital or at another filling station. However, such a filling station is typically located in a remote part of the facility, relative to the patient care area, where the injection is to be administered. Because of the remote location of many nurse's stations, relative to a filling station, a fluid or drug loaded syringe or other medical device is frequently given to another person for delivery to a nurse's station for subsequent dosing of the patient. In the case where a prefilled drug in the syringe is very expensive or addictive such as, but not limited to, morphine, there is a danger of tampering, by a person seeking unauthorized access to the prefilled contents of the syringe or medical device.

If tampering does occur, the potential for serious consequences exists. For example, there is a possibility that the prescribed medicine will be replaced by some other, unauthorized substance. As an illustration of this, if saline solution were substituted for a dose of morphine or other medication, the result could be extremely serious. Thus, there is a problem of knowing if a sealed, pre-loaded syringe or other administering device has, or has not, been compromised by tampering and/or exposed to contamination so that it is no longer sterile.

In addition to the administration of drugs, medicine, etc., meaningful protection is required in the use of enteral feeding sets. As commonly recognized in the medical and related professions, the term "enteral" relates to the administration or removal of fluid to or from the gastrointestinal tract. Moreover, enteral connectors and/or fixtures of the type referred to herein relate to medical devices or accessories which are intended for use in enteral applications. Further, small-bore connectors for enteral application may be employed for delivery of enteral nutrition fluid from a fluid source to the patient. Additionally, it is pointed out that enteral feeding sets and extension sets may include a female fixture, wherein the source of fluid flows to the patient initially through the female fixture and to and through a cooperatively structured male enteral fixture.

Also, with regard to administering fluids to a patient by intravenous (IV) infusion, a variety of IV assemblies are used in the treatment of numerous medical conditions. Different types of connectors, such as a "female" connector may be attached to the discharge end or discharge port of an IV bag or like medical device/container. Such an appropriate female connector may be in the form of a female luer connector which at least partially defines, along with a male luer connector, a "luer lock" connector assembly, as is well known in the medical profession. In periods of non-use, it is important to maintain such connectors associated with an IV facility, in a closed and fluid sealed condition in order to maintain sterility and integrity of the IV fluid prior to use.

Therefore, regardless of the known or conventional attempts to provide a fluid restricting closure to protect the contents of preloaded medical dispensers or administering devices including enteral devices, certain problems still remain in this field of art. Accordingly, there is a need in this area for an improved, closure assembly which provides a secure and reliable fluid restricting or fluid sealing connection to the discharge port, fixture or connector of a medical device of the type set forth herein. If any such improved closure assembly were developed, it would preferably also overcome known disadvantages in the production and/or assembly of conventional closures, including tamper evident closures.

However, in order to do so, any such closure assembly would preferably also include a unique construction to help reduce, if not eliminate, the need for time-consuming, costly and overly complicated production techniques associated with the production of more conventional closures for medical devices. Also, if any such closure assembly were developed, it should further be capable of use with little or no structural modification on a variety of different connectors, fixtures, administering devices, discharge ports, etc. Finally, if any such improved closure assembly were developed, it should also be structurally and operatively reliable, while improving the cost effectiveness associated with the manufacture and assembly thereof.

SUMMARY OF THE INVENTION

The present invention is directed to a closure assembly for a medical dispenser having a discharge port structured and disposed to allow the contents of the medical dispenser to exit in an intended fashion. Accordingly, as used herein the term "discharge port" is meant to include the structure, section, segment and/or component of the medical dispenser through which the content of the dispenser passes, as it is removed from the interior of the medical dispenser. By way of non-limiting example, when the medical dispenser is in the form of a prefilled syringe, the discharge port is meant to include, but not necessarily be limited to, a nozzle, a flow channel within the nozzle, a terminal opening formed in the outer end of the nozzle, through which the contents of the syringe pass upon exiting the interior thereof.

One embodiment of the closure assembly of the present invention includes a tip cap having an access opening and an oppositely disposed closed end. As utilized, the tip cap is operatively disposed in enclosing relation to a discharge port of the medical dispenser and, in at least one embodiment, the tip cap is dimensioned to define a removable, slip-fit attachment to the discharge port. Further, the tip cap is preferably formed from a material having sufficient flexibility to be disposed and/or forced into sealing engagement with the discharge port, once it is operatively disposed in enclosing relation thereto.

Moreover, the flexibility of the tip cap should be sufficient to allow it to be "squeezed" into the aforementioned sealing engagement with the exterior of the discharge port, when an outer clamping force or deformation force is applied to the exterior of the tip cap. The material from which the tip cap is formed may also be accurately defined as being "elastomeric" to the extent that it may be squeezed, stretched or deformed inwardly into sealing engagement with the exterior of the discharge port, concurrent to the exterior clamping force being exerted thereon. As such, the sealing engagement between the tip cap and the discharge port of the medical dispenser may be more specifically defined as the inner surface of the tip cap being disposed in a forced and/or clamped into the sealing engagement with the exterior surface of the discharge port.

A related feature of this embodiment of the closure assembly of the present invention includes its structural dimensioning to have a sufficient interior dimension to be used with and disposed in sealing engagement with discharge ports of different dimensions. The flexibility and/or elastomeric capabilities of the tip cap material further enhance its versatile use, by further facilitating it being mounted on discharge ports of different smaller dimensions. Therefore, the tip cap is removably mounted, by virtue of a slip-fit attachment, in enclosing relation to any one of a possible plurality of discharge ports having a lesser outer dimension, than the interior dimension of the tip cap, by virtue of at least it's dimensioning and flexible, elastomeric capabilities.

As indicated, the sealing engagement between the tip cap and the discharge port, when the closure assembly is operatively disposed, is established by an outer clamping force being exerted on the tip cap. Therefore, this embodiment of the closure assembly also includes a retainer disposed in surrounding, clamping relation to an exterior of the tip cap, concurrent to the tip cap being operatively disposed in enclosing relation to the discharge port. In at least one embodiment, the retainer may include a clamping structure disposed in a clamping relation to the exterior surface of the tip cap in order to establish and define the sealing engagement of the tip cap with the discharge port. In more specific terms, the clamping relation between the retainer and the tip cap define a fluid sealing engagement of the inner surface of the tip cap with the outer surface of the discharge port, concurrent to the tip cap disposed within and/or being clamped by the retainer.

In order to facilitate the exertion of an adequate clamping force, the clamping structure may include at least one or a plurality of rib members. Further, the at least one clamping rib member may be disposed on the retainer in a manner which facilitates the exertion of the aforementioned clamping force on the exterior of the tip cap. Further, with regard to at least one embodiment of the closure assembly, the retainer may be in the form of or comprise a substantially clamshell-like configuration.

The clamshell type of retainer is positioned from an open orientation, during which the tip cap may be inserted, into a closed orientation. Further the clamshell and retainer, when in the closed orientation, is further structured to prevent a reopening thereof due to a cooperative structuring of a locking attachment. As such, the clamshell type of retainer may include the clamping structure comprising the aforementioned at least one rib member, which may include one or more clamping rib sections disposed on the interior surface of the retainer. When the clamshell retainer is fixedly disposed in the closed orientation the one or more clamping rib sections will be disposed in the clamping relation to the exterior of the tip cap and will exert the intended and appropriate clamping force thereon.

It is emphasized that the clamping relation exerted by the retainer on the tip cap initially occurs when the tip cap is disposed in the aforementioned enclosing relation to the discharge port. However, as also indicated, the discharge port and the tip cap are removably connected by virtue of the aforementioned slip-fit attachment therebetween.

Therefore, in order to access the contents of the medical dispenser, syringe, etc., the discharge port is removed from the interior of the tip cap, by exerting a pulling force thereon and/or on the medical dispenser to which it is connected. In a typical application, removal of the discharge port from the tip cap will occur concurrent to the clamping relation being exerted on the tip cap by the retainer and a capturing or maintaining of the tip cap within the retainer. Accordingly, the maintenance of the clamping relation, upon removal of the discharge port from the interior of the tip cap, will result in a further "squeezing" deformation. Such a squeezing deformation may also result in an at least partial closing of the access opening of the tip cap.

As a result, the tip cap will be disposed and/or configured into an orientation and/or position, which will block or otherwise prevent reinsertion of the discharge port into the interior of the tip cap. Therefore, due at least in part to the flexible or elastomeric characteristics of the tip cap, it will be forced into access blocking relation to the discharge port, upon an attempted reinsertion of the discharge port into the tip cap. This inability to reinsert the discharge port into the interior of the tip cap and/or clamping retainer is indicative of unauthorized tampering or authorized access to the contents of the medical dispenser.

Yet another embodiment of the present invention includes a closure assembly having a tip cap which includes an access opening and an oppositely disposed closed end. Further, the tip cap includes an elongated sealing stem including a free end and a base fixedly or integrally secured to an interior of the closed-end. The sealing stem further includes an exterior sealing surface comprising a progressively increasing outer diameter extending from and between the free end and the base thereof. As a result, a fluid sealing engagement between the tip cap and the discharge port of the associated medical dispenser is accomplished by an insertion of the free end of the sealing stem into the interior of the discharge port. The continued advancement of the discharge port along the length of the sealing stem, from the free end towards the base, will result in a portion of an exterior of the sealing surface coming into sealing engagement with a substantially correspondingly dimensioned terminal opening of the nozzle of the discharge port or other interior surface of the discharge port.

Further, the progressively increasing outer diameter of the exterior sealing surface of the sealing stem may be more specifically defined by a plurality of sealing segments, collectively disposed along the length of the sealing stem. Each of the plurality of sealing segments has a progressively larger outer diameter then the next adjacent, proceeding sealing segment, closer to the free end of the sealing stem. Therefore, as the sealing stem passes into the interior of the discharge port, the terminal opening or other portion of the discharge port will eventually engage a correspondingly dimensioned one of the plurality of sealing segments. When so aligned, the aforementioned fluid sealing engagement between the sealing stem and the discharge port will be established.

At least this embodiment of the tip cap, including the elongated sealing stem, may also include structural additions including an outer cover. The cover is disposed in surrounding relation to the tip cap and may include tamper evident characteristics. More specifically, a tether assembly may be disposed in interconnecting relation to the body of the medical dispenser and the cover in a manner which prevents access to the tip cap and the contents of the medical dispenser, without breakage or removal of the tether assembly.

In more specific terms, the tether assembly includes an elongated tether of a high strength material fixedly attached at one end to the medical dispenser. The opposite end of the elongated tether is removably attached to the cover, such as by a frangible connection. Due to the high strength material of the elongated tether and the fact that one end thereof is fixedly attached to the medical dispenser, access to the contents of the medical dispenser and/or the tip cap can only be accomplished by a breakage or separation of the frangible connection between the cover and the corresponding end of the elongated tether. As a result, unauthorized access and/or tampering is evident by a breakage/disconnection of the distal end of the tether from the cover.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

As represented in the accompanying drawings, the present invention is directed to a closure assembly, generally indicated as 10. With initial reference to FIGS. 1 to 4, the closure assembly 10 is illustrated in a first embodiment and comprises a tip cap 12 including an access opening 14 and a closed oppositely disposed end 16. When operatively disposed in an intended manner, the tip cap 12 is positioned in enclosing relation to a discharge port 100 of a medical dispenser 102.

The versatility of the closure assembly 10 is such that it can be used to close the discharge port of different types of medical dispensers. However, for purposes of clarity, the medical dispenser 102, represented throughout at least FIGS. 1-4, is a prefilled syringe, and may include an oral syringe. As such, the discharge port 100 includes, but is not necessarily limited to, a nozzle 104, a flow channel 105 within the nozzle 104 and a terminal opening 106 formed in the outer end of the nozzle 104, through which the contents of the syringe 102 pass, upon exiting the interior of the medical dispenser or syringe 102.

Figure 1:
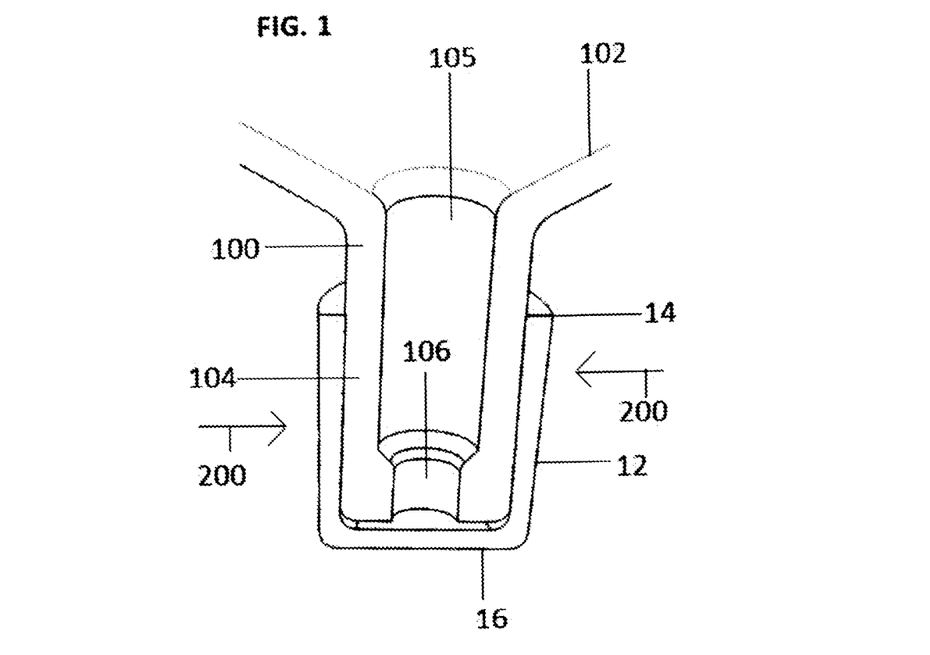
FIG. 1 is an interior perspective view of one embodiment of a tip cap of the closure assembly of the present invention operatively disposed on a discharge port of a medical dispenser.

In the partially assembled, operative disposition of FIG. 1, the tip cap 12 is not necessarily disposed in direct sealing engagement with the discharge port 100. Further, one feature of the tip cap 12 is interiorly dimensioned to accommodate any one of a plurality of discharge ports, which have a sufficiently smaller dimension to fit within the interior of the tip cap 12. Therefore, the tip cap 12 is dimensioned to define a removable, slip-fit attachment to the discharge port 100. Further, the tip cap 12 is preferably formed of a material having sufficient flexibility to be disposed, minimally deformed and/or forced into sealing engagement with the discharge port 100, once it is positioned in the operative disposition of FIGS. 1, 3 and 4.

Moreover, the flexibility of the tip cap 12 should be sufficient to allow it to be "squeezed" inwardly as schematically illustrated by arrows 200 representing a squeezing force, into sealing engagement with the exterior of the discharge port 100, when the outer clamping or deformation force 200 is applied to the exterior of the tip cap 12. In order to establish a fluid sealing connection between the inner surface of the tip cap 12 and the outer surface of the discharge port 100 and/or nozzle 104, the material from which the tip cap 12 is formed may also be accurately described as "elastomeric". The "elastomeric" capabilities of the tip cap 12 facilitate it being squeezed or at least minimally deformed inwardly into the aforementioned fluid sealing engagement with the exterior of the discharge port 100, concurrent to the exterior clamping force 200 being exerted on the exterior of the tip cap 12. As such, the fluid sealing engagement between the tip cap 12 and the discharge port 100 of the medical dispenser 102 may be more specifically and accurately described as the inner surface of the tip cap 12 being disposed in a forced and/or clamped, fluid sealing engagement with the exterior surface of the discharge port 100.

As set forth above, a related feature of the embodiment of FIGS. 1-4 includes its structural dimensioning to have a sufficient interior dimension to be used with and disposed in sealing engagement with discharge ports of different lesser dimensions. The flexibility and/or elastomeric capabilities of the tip cap 12 further enhance its versatile use, by further facilitating it being mounted on discharge ports 100 of different smaller dimensions. Therefore, the tip cap 12 is removably mounted, by virtue of a slip-fit attachment, as represented in FIG. 1, in enclosing relation to any one of a possible plurality of discharge ports having a lesser outer dimension, than the interior dimension of the tip cap 12. Therefore, the removable slip-fit attachment of the tip cap 12 on the discharge port 100 and/or nozzle 104 thereof is facilitated because of the above noted preferred dimensioning as well as its flexible, elastomeric characteristics.

Figure 2:
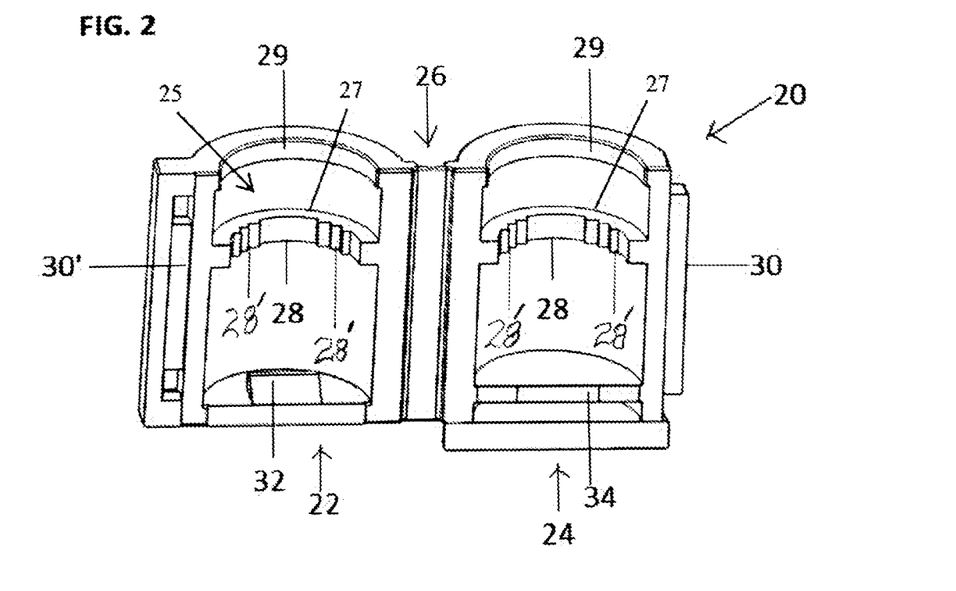
FIG. 2 is an interior perspective view of a retainer used in combination with the tip cap of the embodiment of FIG. 1 and considered a part of the closure assembly of the present invention.
Figure 3:
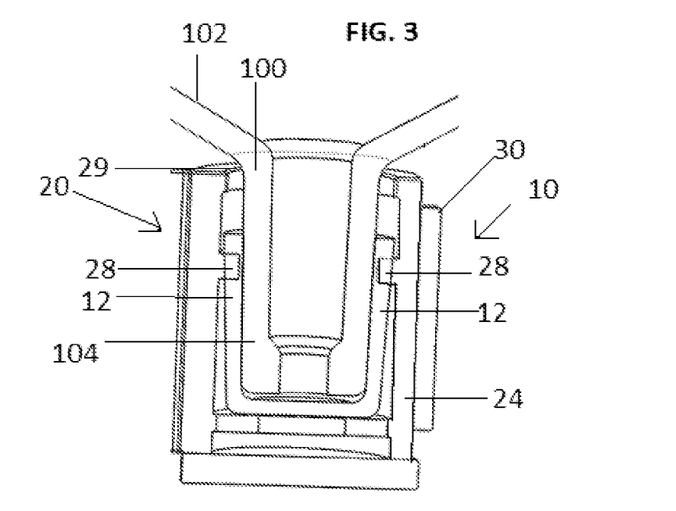
FIG. 3 is an interior sectional view of an assembled and operatively disposed closure assembly of the embodiments of FIGS. 1 and 2, relative to the discharge port of the medical dispenser.
Figure 4:
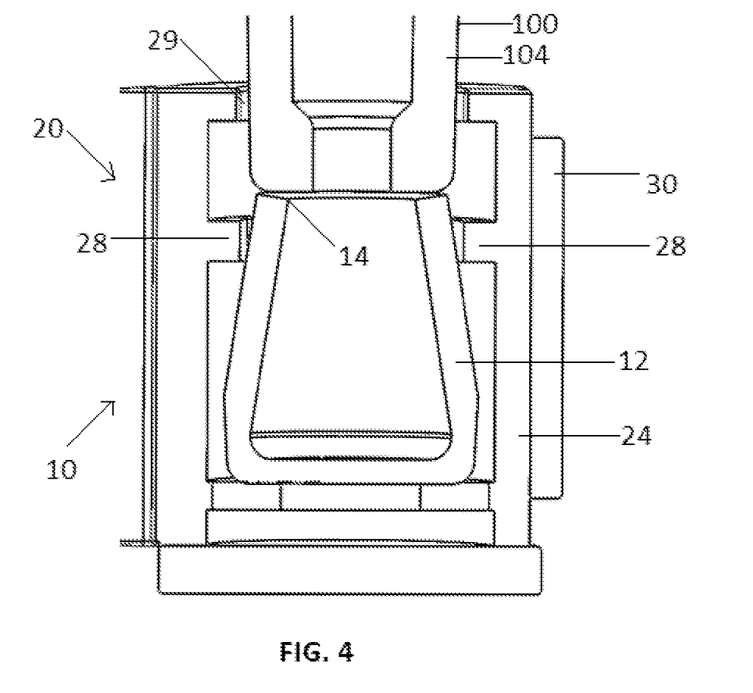
FIG. 4 is an interior sectional view of the embodiment of FIG. 3 representing an attempted reinsertion of the discharge port into the closure assembly of the embodiment of FIGS. 1-3, subsequent to its removal.

Accordingly, in order to establish the inwardly directed, squeezing and/or clamping force 200 on the exterior of the tip cap 12, the closure assembly 10 of the present invention includes a retainer. As represented in FIGS. 2-4, one embodiment of the retainer is generally indicated as 20 and may include a substantially clamshell-like structural configuration. Moreover, the clamshell structuring of the retainer 20 includes two segments 22 and 24 pivotally or movably connected by a hinge segment 26 therefore, the retainer segments 22 and 24 may be selectively disposed from the open position of FIG. 2, to the closed position as represented in FIGS. 3 and 4. As should be apparent, when in the open orientation of FIG. 2, the retainer 20 may be disposed in surrounding, enclosing relation to the exterior of the tip cap 12, concurrent to the tip cap 12 disposed in surrounding relation to the discharge port 100. When operatively disposed, the retainer may then be selectively positioned in the closed orientation of FIGS. 3 and 4.

Additional structural features of the retainer 20 are represented in at least FIG. 2 and include a clamping structure 25 comprising at least one rib member 27. The rib member 27 includes a plurality of at least two clamping rib sections 28. Each of the clamping rib sections 28 is formed on the interior surface of a different one of the two retainer segments 22 and 24, in substantially opposing relation to one another. Further, each of the two clamping rib sections 28 extend outwardly from the respective interior surfaces of the retainer segments 22 and 24 and are movable therewith between the open and closed orientations. As further represented in FIG. 2, each clamping rib section 28 includes an irregular surface configuration 28'. Also, the retainer 20 includes a locking connection or fixtures 30 and 30' which are cooperatively structured to fixedly engage one another and thereby maintain and lock the retainer 20 in the closed orientation. Also, when in the closed orientation the retainer 20 includes an open end defined by the open ends 29 of the retainer segments 22 and 24. As a result, when in the locked, closed orientation access to the tip cap 12, while it is enclosing the discharge port 12, cannot be accomplished without a breaking, damaging or destroying the retainer 20. Maintenance of the retainer 20 in the closed orientation may be further facilitated by a ramp and recess structure 32 and 34 respectively formed on the different retainer segments 22 and 24.

With primary reference to FIGS. 3 and 4, when in the locked, closed orientation, the retainer 20 exerts the aforementioned inwardly directed squeezing and/or clamping force 200 on the exterior of the tip cap 12. Such a squeezing or clamping force 200 may be facilitated by structuring the clamping ribs 28 to define an opening, in which the tip cap 12 is disposed, having a lesser dimension than that of the access opening 29 of the retainer 20, when in the closed orientation, as clearly represented.

Due to the removable, slip-fit connection between the tip cap 12 and the discharge port and/or nozzle 104, access to the contents of the medical dispenser 102 can only be effectively accomplished by removing the discharge port 100 from the interior of the tip cap 12 and the retainer 20 while the tip cap remains within the retainer. This is accomplished by exerting a separating, pulling force on the medical dispenser 102 or exterior of the retainer 20, or both. However, upon removal of the discharge port 100 through the access opening 29 of the retainer and access opening 14 of the tip cap 12, the squeezing and/or clamping force 200 will continue to be exerted on the exterior of the tip cap 12 and a capturing of the tip cap 12 within the retainer 20, as represented in FIG. 4.

This continued exertion of the squeezing and/or clamping force 200 on the tip cap 12 will result in an additional inward deformation of the tip cap 20 and at least a partially closing orientation of the access opening 14 of the tip cap 12. As a result, reinsertion of the discharge port 100 will be prevented due to the additional inward deformation of the tip cap 12 and/or closing orientation of the access opening 14 as clearly represented in FIG. 4. Therefore, the tip cap 12 is disposed in an insertion blocking position, which prevents reinsertion of the discharge port into the interior of the tip cap 12.

Figure 5:
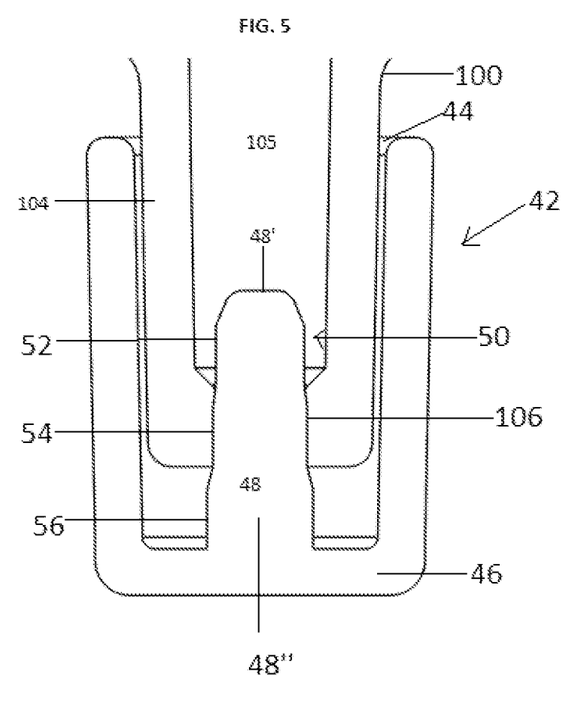
FIG. 5 is an interior sectional view of an additional embodiment of a tip cap of the closure assembly of the present invention.
Figure 6:
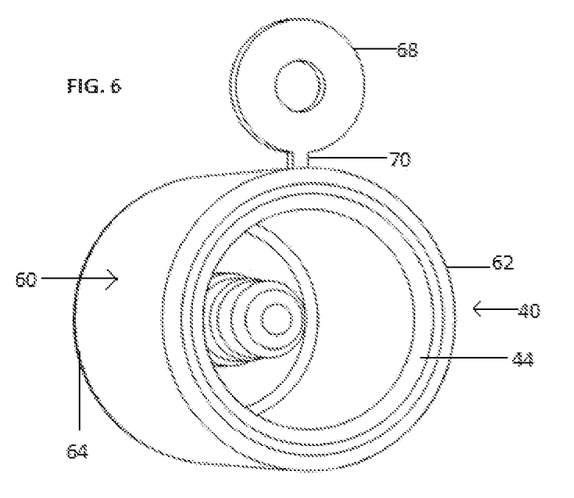
FIG. 6 is a perspective interior view of the tip cap of the embodiment of FIG. 5, at least partially assembled with a cover.

As represented in at least FIGS. 5 and 6, yet another embodiment of the present invention includes a closure assembly 40 including a tip cap 42 comprising an access opening 44 and an oppositely disposed closed end 46. Further, the tip cap 42 includes an elongated sealing stem 48 including a free end 48' and a base 48'', wherein the base 48'' is fixedly or integrally secured to an interior of the closed-end 46. The sealing stem 48 further includes an exterior sealing surface 50 comprising a progressively increasing outer diameter extending from and between the free end 48' and the base 48'' thereof. As a result, a fluid sealing engagement between the tip cap 42 and the discharge port 100 of the associated medical dispenser 102 is accomplished by an insertion of the free end 48' of the sealing stem 48 into the interior of the flow path 105 of the discharge port 100. The continued advancement of the nozzle 104 of the discharge port 100 along the length of the sealing stem 48 and outer sealing surface 50, from the free end 48' towards the base 48'', will result in sealing engagement therebetween. In more specific terms, as the sealing stem 48 advances into the nozzle 104 through the flow path 105, a portion of an exterior of the sealing surface 50 will eventually come into sealing engagement with a substantially correspondingly dimensioned portion of the discharge port 100, such as the terminal opening 106.

Further, the progressively increasing outer diameter of the exterior sealing surface 50 of the sealing stem 48 may be more specifically defined by a plurality of sealing segments 52, 54, 56, etc., collectively disposed along the length of the sealing stem 48. It is emphasized that the number of sealing segments 52, 54, 56, etc. may vary in order to increase the versatility of the tip cap 42, at least in terms of establishing a fluid sealing engagement with discharge ports of different sizes, configurations, categories, etc.

In addition, each of the plurality of sealing segments 52, 54, 56, etc. preferably has a progressively larger outer diameter than the next adjacent, preceding sealing segment, which is closer to the free end 48' of the sealing stem 48. Therefore, as the sealing stem 48 passes into the interior of the flow channel 105 of the discharge port 100, the terminal opening 106 or other portion of the discharge port 100 will eventually engage a substantially correspondingly dimensioned one of the plurality of sealing segments 52, 54, 56, etc. When so aligned, the aforementioned fluid sealing engagement between the outer sealing surface 50 of the sealing stem 48 and the discharge port 100 will be established. Therefore, the operative disposition of the tip cap 42 relative to the discharge port 100 is its disposition in surrounding substantially enclosing relation to at least a portion of the nozzle 104 and terminal opening 106, as clearly represented in FIG. 5.

As represented in FIG. 6, the closure assembly 40 of this embodiment may also include structural additions including an outer cover 60. The cover 60 is operatively disposed in enclosing, surrounding relation to the tip cap 42 and may include an access opening 62 and a closed end 64. Further, the cover 60 may be structured to have tamper evident characteristics. More specifically, a tab 68 is frangibly or otherwise removably connected to the cover 60, as at 70. In cooperation therewith, a tether assembly generally indicated as 80 in FIG. 7, may be concurrently disposed in interconnecting relation to the body 102' of the medical dispenser 102 and the cover 60. In more specific terms, the tether assembly 80 includes an elongated high strength tether 82 having one end 82' connected to an attachment structure 84. The opposite end of the elongated tether 82 is connected to the cover 60 via direct attachment to the tab 68.

Figure 7:
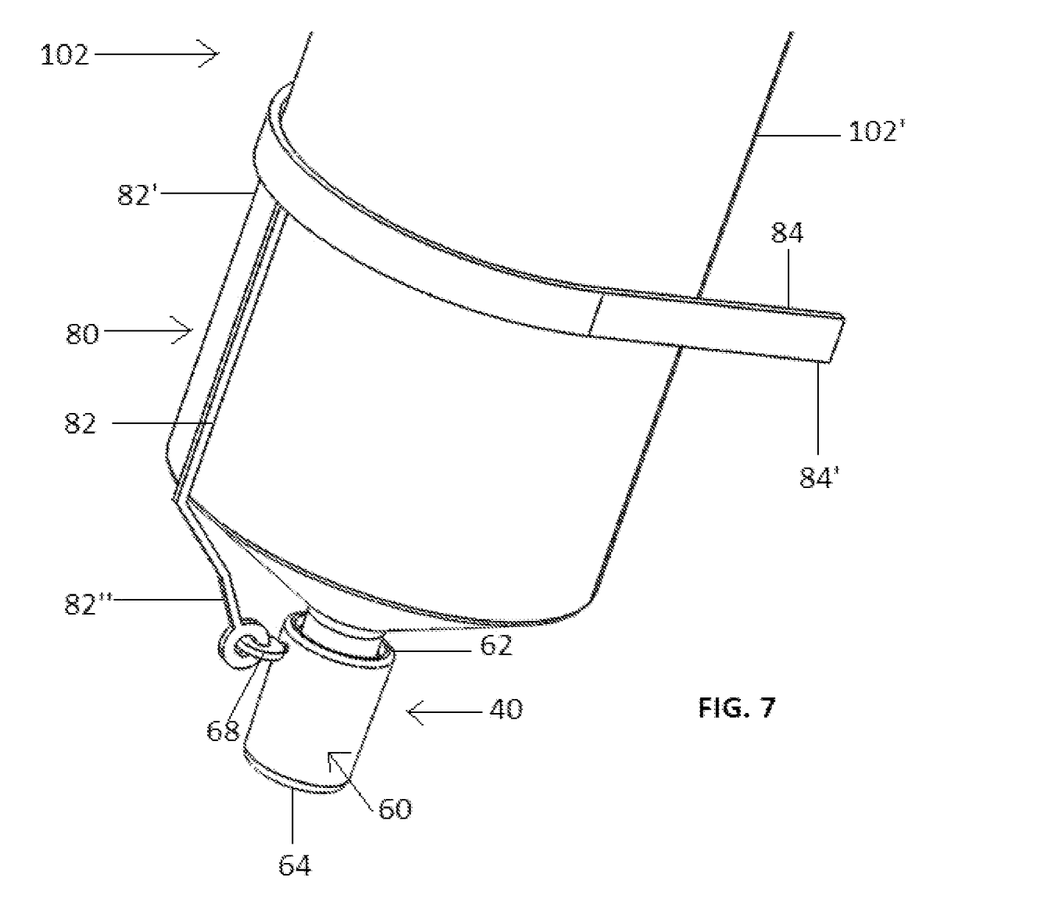
FIG. 7 is a perspective view of the embodiment of FIGS. 5 and 6 operatively disposed in connected relation to a medical dispenser and including tamper evident characteristics.

The attachment structure 84 may assume a variety of different structural and operative features which facilitate a fixed, generally non-removable attachment to the body 102' of the medical dispenser 102. Further, the attachment structure 84 may have a fixed, locking connector as at end 84' and/or be adhesively attached to the exterior surface of the body 102' of the medical dispenser 102. Also, the length of the tether 82 relative to the dispositions of the attachment member 84 and closure assembly 40 limits or restricts removal of the cover 60 from the tip cap 42 without a breaking, cutting, or other destructive removal of the tether 82 and/or the attachment member 84.

However, as set forth above, one end 82" of the tether 82 is removably connected to the cover 60 via the frangible or removably connected tab 68. Due to the high strength material of the tether 82 and the fixed attachment of the attachment member 84 to the body 102' of the medical dispenser 102, attempted access to the tip cap 42 and the contents of the medical dispenser 102 will most probably result in a breakage of the frangible connection 70. This, in turn, will result in a disconnection of the tab 68 and the tether 82 from the cover 60. Such breakage, disconnection or removal of the tab 68 will provide a clear indication of attempted tampering and/or authorized access to the closure assembly 40 and contents of the medical dispenser 102.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A closure assembly for a medical dispenser, said closure assembly comprising:
    a tip cap at least partially formed of an elastomeric material and including an access opening and an oppositely disposed closed end,
    said tip cap operatively disposed in a removable, enclosing relation to a discharge port of the medical dispenser,
    a retainer comprising a clamshell configuration including two retainer segments movably connected to one another and disposable between an open orientation and a closed orientation,
    said retainer disposed in surrounding relation to said tip cap concurrent to said closed orientation of said two retainer segments,
    a clamping structure comprising at least one rib member, said at least one rib member including two rib sections, each of said two rib sections formed on an interior surface of a different one of said two retainer segments,
    said two rib sections movable with said different one of said two retainer segments, between said open orientation and said closed orientation,
    said two rib sections disposed in a deforming, clamping relation to an exterior of said tip cap, concurrent to said closed orientation of said two retainer segments,
    said deforming, clamping relation of said two rib sections on said tip cap defining a fluid sealing engagement of said tip cap with the discharge port, concurrent to said tip cap and the discharge port disposed within said retainer, and
    said closed orientation further comprising a capturing relation of said tip cap within said retainer concurrent to removal of the discharge port from said tip cap and said retainer,
    said deforming, clamping relation further comprising a deformation of said tip cap into an insertion blocking relation to said access opening, concurrent to removal of the discharge port from said tip cap.

2. The closure assembly as recited in claim 1 wherein said tip cap is dimensioned and configured to define a removable, slip-fit connection of the discharge port within said tip cap.

3. The closure assembly as recited in claim 1 wherein said two rib sections are disposed in substantially opposed, concurrently clamping engagement with said tip cap, concurrent to said deforming, clamping relation of said retainer relative to said tip cap.

4. The closure assembly as recited in claim 1 wherein said tip cap includes an interior dimension sufficient to enclose any one of a plurality of smaller dimensioned discharge ports.

5. The closure assembly as recited in claim 1 wherein said tip cap is at least partially formed of a material, of sufficient flexibility, to dispose an interior surface of said tip cap into said fluid sealing engagement with an exterior surface of the discharge port, concurrent to said deforming, clamping relation.

6. A closure assembly for a medical dispenser, said closure assembly comprising:
    a tip cap at least partially formed of an elastomeric material and including an access opening and an oppositely disposed closed end,
    said tip cap operatively disposed in enclosing relation to a discharge port of the medical dispenser,
    a retainer comprising a clamshell configuration including two retainer segments movably connected to one another and disposable between an open orientation and a closed orientation,
    said retainer disposed in surrounding relation to said tip cap concurrent to said closed orientation of said two retainer segments,
    a clamping structure comprising at least one rib member, said at least one rib member including two rib sections, each of said two rib sections formed on an interior surface of a different one of said two retainer segments,
    said two rib sections disposed in a deforming, clamping relation to an exterior of said tip cap, concurrent to said closed orientation of said two retainer segments,
    said deforming, clamping relation comprising a fluid sealing engagement of said tip cap with the discharge port, concurrent to said tip cap and the discharge port disposed within said retainer,
    said two rib sections disposed to capture said tip cap within said retainer in said deforming, clamping relation therewith, concurrent to removal of the discharge port from said tip cap and said retainer,
    said deforming, clamping relation by said two rib sections further comprising a deformation of said tip cap into an insertion blocking relation to said access opening, concurrent to the removal of the discharge port from said tip cap and said retainer, and said deformation of said tip cap into said insertion blocking relation to said access opening further comprising an at least partial closure of said access opening.

7. The closure assembly as recited in claim 6 wherein said tip cap is at least partially formed of a material, of sufficient flexibility, to dispose an interior surface of said tip cap into said fluid sealing engagement with an exterior surface of the discharge port, concurrent to said deforming, clamping relation.

8. The closure assembly as recited in claim 6 wherein said tip cap is dimensioned and configured to define a removable, slip-fit connection of the discharge port within said tip cap.

9. The closure assembly as recited in claim 6 wherein said at least partial closure of said tip cap comprises a retaining, capturing engagement by said retainer with said tip cap, concurrent to removal of the discharge port from said tip cap.

10. The closure assembly as recited in claim 6 wherein said tip cap includes an interior dimension sufficient to enclose any one of a plurality of smaller dimensioned discharge ports.

\* \* \* \* \*